US00PP21239P2

(12) United States Plant Patent
Merz

(10) Patent No.: US PP21,239 P2
(45) Date of Patent: Aug. 24, 2010

(54) ***CORTADERIA* PLANT NAMED 'GOLDEN GOBLIN'**

(50) Latin Name: *Cortaderia selloana*
Varietal Denomination: Golden Goblin

(76) Inventor: Michael Merz, Rohrstrasse 400, D-63075 Offenbach (DE)

( * ) Notice: Subject to any disclaimer, the term of this patent is extended or adjusted under 35 U.S.C. 154(b) by 0 days.

(21) Appl. No.: 12/383,846

(22) Filed: Mar. 27, 2009

(51) Int. Cl.
*A01H 5/00* (2006.01)

(52) U.S. Cl. ..... Plt./384

(58) Field of Classification Search ..... Plt./384
See application file for complete search history.

(56) References Cited

OTHER PUBLICATIONS

Plant Variety Database 2009/06 search for Golden Goblin.*

* cited by examiner

*Primary Examiner*—Annette H Para
(74) *Attorney, Agent, or Firm*—C.A. Whealy

(57) ABSTRACT

A new and distinct cultivar of *Cortaderia* plant named 'Golden Goblin', characterized by its compact, upright to outwardly arching plant habit; green and yellow variegated leaves; early flowering habit; and good garden performance.

3 Drawing Sheets

Botanical designation: *Cortaderia selloana.*
Cultivar denomination: 'GOLDEN GOBLIN'.

BACKGROUND OF THE INVENTION

The present invention relates to a new and distinct cultivar of *Cortaderia* plant, botanically known as *Cortaderia selloana*, and hereinafter referred to by the name 'Golden Goblin'.

The new *Cortaderia* plant is a naturally-occurring branch mutation of *Cortaderia selloana* 'Pumila', not patented. The new *Cortaderia* was discovered and selected by the Inventor within a population of plants of 'Pumila' in a controlled outdoor nursery environment in Offenbach, Germany during the summer of 2001.

Asexual reproduction of the new *Cortaderia* plant by divisions in Offenbach, Germany since the autumn of 2005, has shown that the unique features of this new *Cortaderia* plant are stable and reproduced true to type in successive generations.

SUMMARY OF THE INVENTION

Plants of the new *Cortaderia* have not been observed under all possible environmental conditions. The phenotype may vary somewhat with variations in environment such as temperature and light intensity, without, however, any variance in genotype.

The following traits have been repeatedly observed and are determined to be the unique characteristics of 'Golden Goblin'. These characteristics in combination distinguish 'Golden Goblin' as a new and distinct cultivar of *Cortaderia:*

1. Compact, upright to outwardly arching plant habit.
2. Green and yellow variegated leaves.
3. Early flowering habit.
4. Good garden performance.

Plants of the new *Cortaderia* differ from plants of the parent, 'Pumila', in the following characteristics:

1. Plants of the new *Cortaderia* are more compact than plants of 'Pumila'.

2. Leaves of plants of the new *Cortaderia* are green and yellow variegated whereas leaves of plants of 'Pumila' are green in color.
3. Plants of the new *Cortaderia* are more freely flowering than plants of 'Pumila'.

Plants of the new *Cortaderia* can be compared to plants of the *Cortaderia selloana* 'Splendid Star', disclosed in U.S. Plant Pat. No. 16,277. Plants of the new *Cortaderia* differ primarily from plants of 'Splendid Star' in plant form as plants of 'Splendid Star' are more outwardly arching than plants of the new *Cortaderia.* In addition, leaf color of plants of the new *Cortaderia* is less intense than leaf color of plants of 'Splendid Star'.

BRIEF DESCRIPTION OF THE PHOTOGRAPHS

The accompanying photographs illustrate the overall appearance of the new *Cortaderia* plant. The photographs show the colors as true as it is reasonably possible to obtain in colored reproductions of this type. Colors in the photographs may differ slightly from the color values cited in the detailed botanical description which accurately describe the colors of the new *Cortaderia* plant.

The photograph on the first sheet comprises a side perspective view of a typical flowering plant of 'Golden Goblin' grown in an outdoor nursery.

The photograph on the second sheet is a close-up view of typical leaves of 'Golden Goblin'.

The photograph on the third sheet is a close-up view of a typical inflorescence of 'Golden Goblin'.

DETAILED BOTANICAL DESCRIPTION

The aforementioned photographs and following observations and measurements describe plants grown in Offenbach, Germany during the autumn in an outdoor nursery and under conditions and practices which approximate those generally used in commercial *Cortaderia* production. During the production of the plants, day temperatures ranged from 10° C. to 25° C. and night temperatures ranged from 2° C. to 14° C.

Measurements and numerical values for represent averages for typical two-year old plants. In the following description, color references are made to The Royal Horticultural Society Colour Chart, 2001 Edition, except where general terms of ordinary dictionary significance are used.

Botanical classification: *Cortaderia selloana* 'Golden Goblin'.

Parentage: Naturally-occurring branch mutation of *Cortaderia selloana* 'Pumila', not patented.

Propagation:

*Type.*—By divisions.

Time to initiate roots, summer.—About one month at 20° C.

*Time to produce a rooted young plant, summer.*—About six months at 20° C.

*Root description.*—Medium in thickness; strongly fibrous; white, close to 155A, in color.

*Rooting habit.*—Moderately branching; dense.

Plant description:

*Plant form/growth habit.*—Herbaceous perennial; compact, upright to outwardly arching plant habit; broadly inverted triangle with arching leaves and upright flower panicles; moderately vigorous growth habit.

*Plant height, including flower panicles.*—About 86 cm.

*Plant height, excluding flower panicles.*—About 79 cm.

*Plant diameter or spread.*—About 109 cm.

*Culm (stem) description.*—Quantity per plant: About 35. Shape: Cylindrical; enclosed by leaf sheaths. Length: About 12.2 cm. Diameter: About 6 mm Internode length: About 2 mm. Aspect: Mostly upright. Strength: Strong. Texture: Smooth, glabrous. Color: Close to 150D, base tinged with close to 182B.

Foliage description:

*Arrangement.*—Alternate, two-ranked, simple; leaf base sheathing the culm.

*Length (including sheath).*—About 90.a cm.

*Width.*—About 7 mm.

*Shape.*—Lanceolate; narrow.

*Apex.*—Long acuminate.

*Margin.*—Entire with short teeth; teeth inconspicious.

*Aspect.*—Initially upright then outwardly arching with development.

*Texture, upper and lower surfaces.*—Mostly smooth.

*Venation pattern.*—Parallel.

*Color.*—Developing leaves, upper surface: Close to 154D; at the margins and longitudinal stripes, close to 138B. Developing leaves, lower surface: Close to 154C to 154D; at the margins and longitudinal stripes, close to 138B. Fully expanded leaves, upper surface: Between 2D and 4D; at the margins, close to 138A; venation, same as leaf blade colors. Fully expanded leaves, lower surface: Close to 150D; at the margins, close to 138A; venation, same as leaf blade colors.

Inflorescence description:

*Arrangement.*—Numerous single flowers arranged in terminal panicles; flowers face upright to slightly outwardly.

*Fragrance.*—None detected.

*Inflorescence length.*—About 32.2 cm.

*Inflorescence diameter.*—About 8 cm.

*Quantity of flowers per inflorescence.*—About 10,000.

*Time to flower.*—From late August to late October in Germany. Individual flowers last about ten days on the plant; flowers persistent.

*Flower buds.*—Length: About 4 mm. Diameter: About 1 mm. Shape: Lanceolate. Color: Close to 145B to 145C; glumes and lemma, between 196D and 197D.

*Flower diameter.*—About 2 mm.

*Flower height.*—About 4 mm.

*Glume/lemma.*—Quantity/arrangement: One glume per flower positioned at posterior of flower with 50 lemma in a circle; glume and lemma enclose immature anthers. Glume length: About 1.6 cm. Glume width: About 0.5 mm. Lemma length: About 1.6 cm. Lemma width: About 0.1 mm. Shape: Glume, linear; lemma, fibril-shaped. Apex, glume and lemma: Narrowly acute. Margin, glume and lemma: Entire. Texture, glume and lemma: Smooth, glabrous. Color, glume and lemma, when opening: Close to 196D. Color, glume and lemma, fully opened: Close to 196C to 196D; color becoming closer to 161D with development.

*Peduncles.*—Length: About 55.2 cm. Diameter: About 7 mm. Strength: Strong. Angle: Erect. Color: Between 4D and 8D.

*Pedicels.*—Length: About 2 mm. Diameter: About 0.5 mm. Strength: Strong. Angle: About 5° from vertical. Color: Close to 145D.

*Reproductive organs.*—Androecium: Stamen quantity per flower: About two. Anther length: About 1.2 mm. Anther shape: Narrowly oblong. Anther color: Close to 145D. Pollen amount: Scarce. Pollen color: Close to 165C. Gynoecium: Not observed.

*Seed/fruit.*—Seed and fruit development have not been observed.

Disease/pest resistance: Plants of the new *Cortaderia* have not been shown to be resistant to pathogens and pests common to *Cortaderia*.

Garden performance: Plants of the new *Cortaderia* have been observed to have good garden performance and to tolerate wind and rain. Plants of the new *Cortaderia* are suitable for USDA Hardiness Zone 7 and USDA Heat Zone 9.

It is claimed:

1. A new and distinct *Cortaderia* plant named 'Golden Goblin' as illustrated and described.

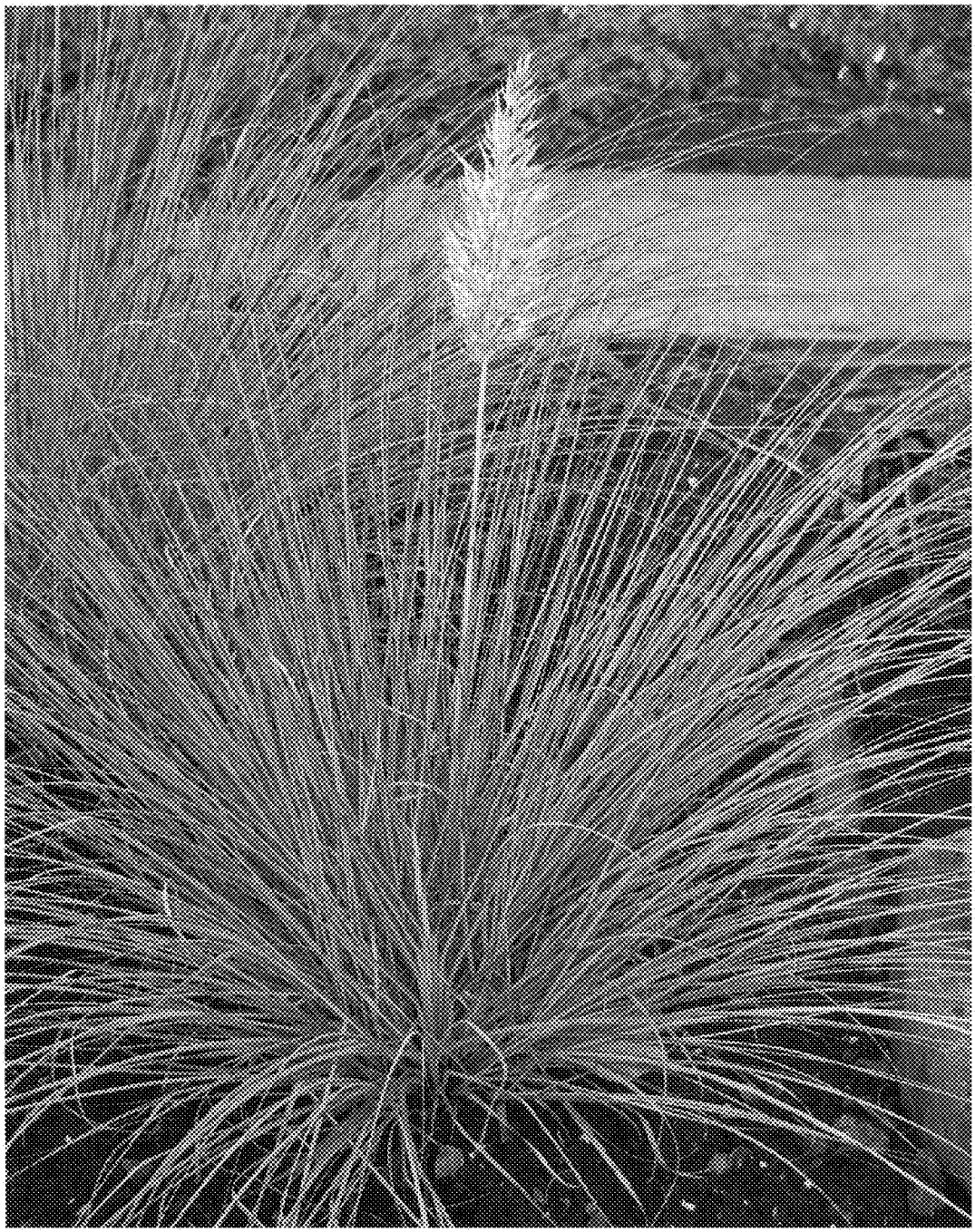

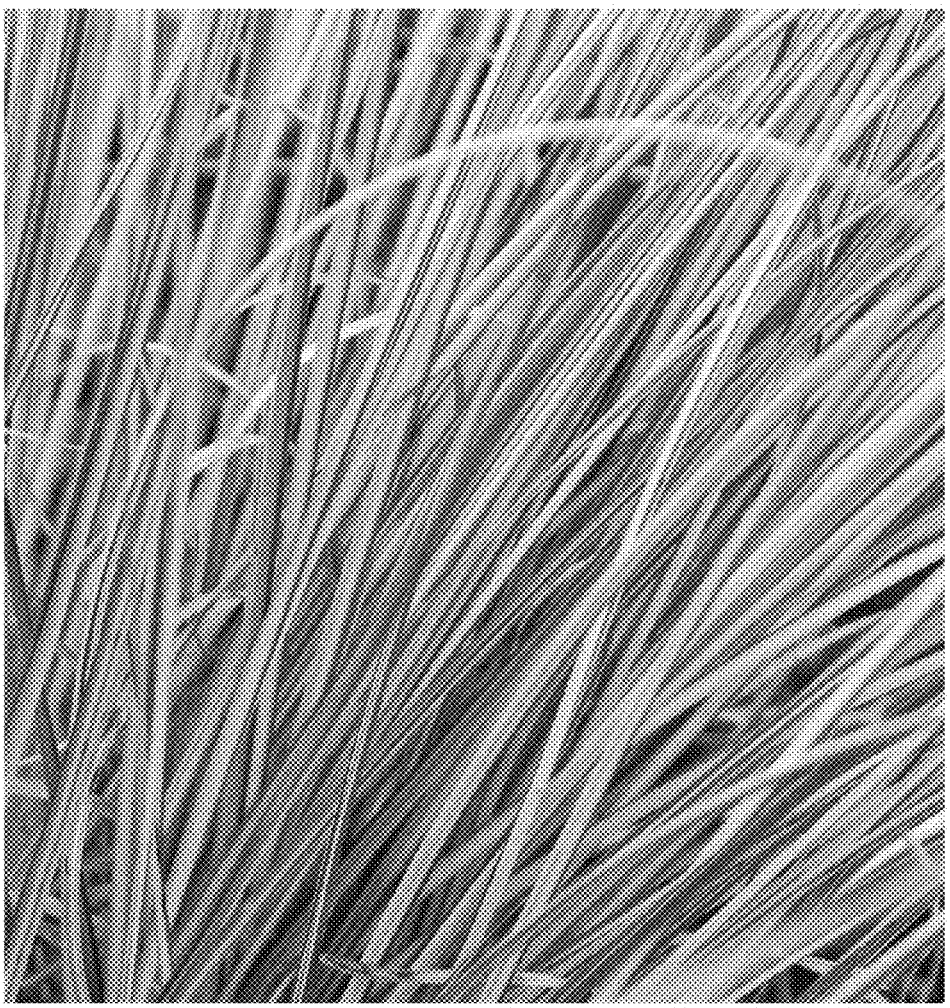

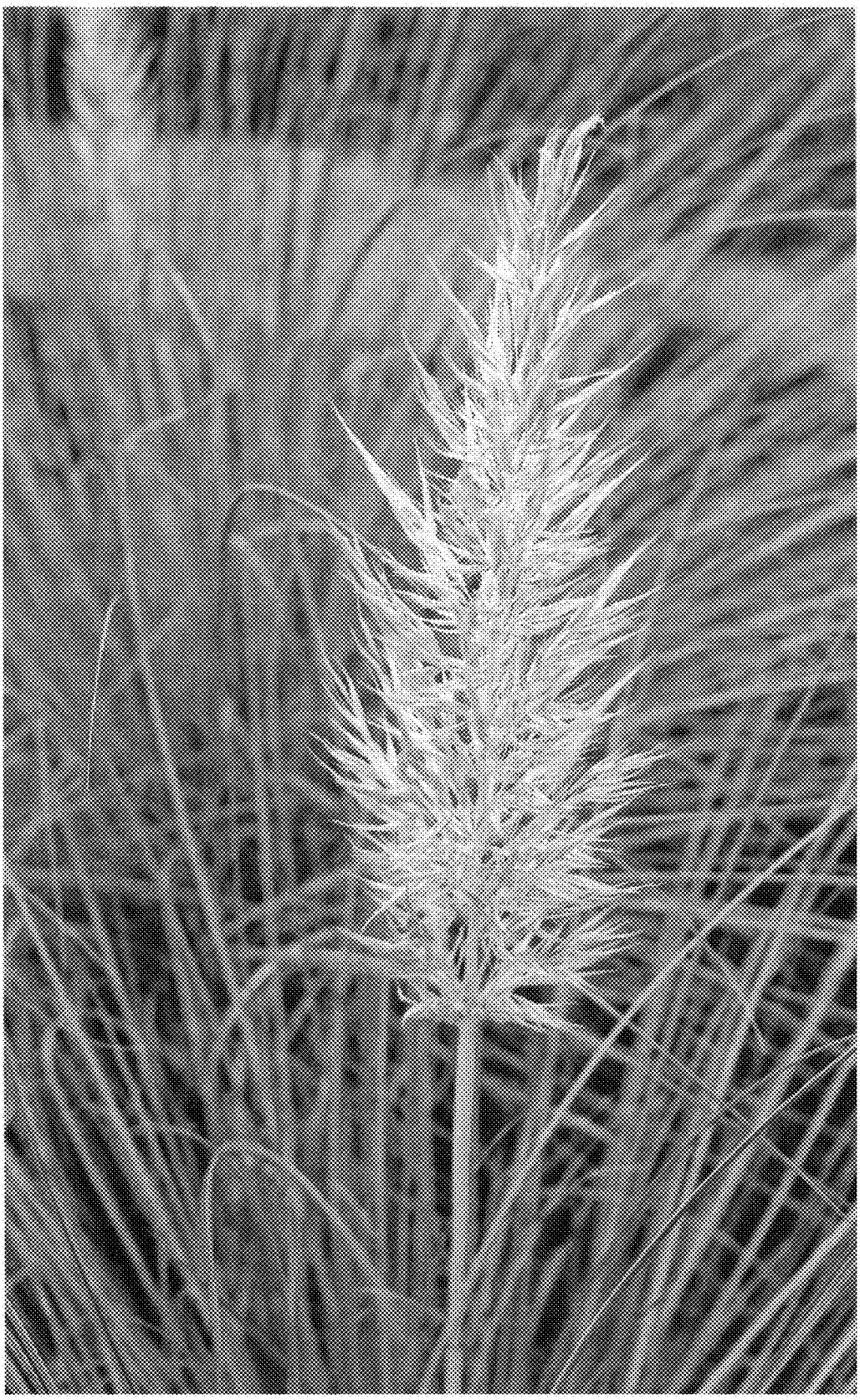

* * * * *